United States Patent
Nam et al.

(10) Patent No.: US 8,758,769 B2
(45) Date of Patent: Jun. 24, 2014

(54) **COMPOSITION FOR PREVENTING AND TREATING ACETAMINOPHEN INDUCING LIVER INJURY COMPRISING THE PROTEIN EXTRACT FROM *PORPHYRA YEZOENSIS***

(75) Inventors: Taek-Jeong Nam, Busan (KR); Mi-Jin Kwon, Busan (KR); Hye-Jung Hwang, Busan (KR)

(73) Assignee: Pukyong National University Industry Academic Cooperation Foundation, Busan (KR)

( * ) Notice: Subject to any disclaimer, the term of this patent is extended or adjusted under 35 U.S.C. 154(b) by 1544 days.

(21) Appl. No.: 12/083,195

(22) PCT Filed: Aug. 28, 2007

(86) PCT No.: PCT/KR2007/004132
§ 371 (c)(1),
(2), (4) Date: Apr. 7, 2008

(87) PCT Pub. No.: WO2008/054057
PCT Pub. Date: May 8, 2008

(65) Prior Publication Data
US 2010/0152422 A1    Jun. 17, 2010

(30) Foreign Application Priority Data
Nov. 2, 2006 (KR) .................... 10-2006-0107896

(51) Int. Cl.
*A61K 36/02* (2006.01)
*A61K 8/97* (2006.01)

(52) U.S. Cl.
CPC .............. *A61K 8/975* (2013.01); *Y10S 435/814* (2013.01); *Y10S 514/893* (2013.01)
USPC ....... 424/195.17; 424/725; 435/814; 514/893

(58) Field of Classification Search
None
See application file for complete search history.

(56) References Cited

U.S. PATENT DOCUMENTS 6,217,879 B1    4/2001  Suetsuna et al.
6,281,222 B1 *  8/2001  Salzman et al. .............. 514/269
2004/0047895 A1 *  3/2004  Hagino et al. ................ 424/439

FOREIGN PATENT DOCUMENTS

JP    63215610 A    *    3/1987

OTHER PUBLICATIONS

Gao et al., Isolation and Characterization of Photosystem II of *Porphyra yezoensis* Ueda, 2004, Acta Biochimica et Biophysica Sinica, 36: 780-785.*
Takahashi et al., Emulsifying Ability of Porpyran Prepared from Dried Nori, *Porphyra yezoensis*, a red Alga, 2000, J Agric Food Chem, 48: 2721-2725.*
Jung et al., Effect on Rat Serum and Liver Enyzme Activity and Murine immunological Function of a Diet containing the Lave polysaccharide porphyran, 2002, Korean J Food Sci and Tech, 34: 325-329.*
Zhao et al., Degradation of porphyran from *Porphyra haitanensis* and the antioxidant activities of the degraded porphyrans with different molecular weight, 2006, International J Biological Macromolecules, 38: 45-50.*
Gilani et al., Protective effect of *Artemisia scoparia* extract against acetaminophen-induced hepatotoxicity, 1993, General Pharmacology, 24: 1455-1458.*
Jung, K.J et al., Korean. J. Food Sci. Technol., 2002, vol. 34, No. 2, pp. 325-329.
Balaji Raghavendran et al., World J. Gastroenterol., Jun. 2006, vol. 12, No. 24, pp. 3829-3834.

* cited by examiner

*Primary Examiner* — Amy L Clark
*Assistant Examiner* — Catheryne Chen
(74) *Attorney, Agent, or Firm* — Birch, Stewart, Kolasch & Birch, LLP

(57) ABSTRACT

Disclosed is a composition for preventing and treating acetaminophen induced liver injury including the protein extracted from *Porphyra yezoensis*. The protein(s), separated and purified from hot water extracts of *Porphyra yezoensis*, having the molecular weight of 14 kDa measured by sodium dodecyl sulfate polyacrylamide gel electrophoresis, has an excellent effect for inhibiting the oxidative injury of liver tissue and cell apoptosis of liver cells induced by acetaminophen.

1 Claim, 5 Drawing Sheets
(4 of 5 Drawing Sheet(s) Filed in Color)

control

AAP treatment group    AAP +seaweeds extracts group (A) control    (B) AAP treatment group    (C) AAP+seaweeds extracts group (A)

(B)

COMPOSITION FOR PREVENTING AND TREATING ACETAMINOPHEN INDUCING LIVER INJURY COMPRISING THE PROTEIN EXTRACT FROM *PORPHYRA YEZOENSIS*

TECHNICAL FIELD

The present invention relates to a composition for preventing and treating acetaminophen induced liver injury comprising the protein extracts from *porphyra yezoensis*. In detail, the present invention relates to a composition for preventing and treating the liver injury comprising the protein, as an effective component, separated and purified from hot water extracts of *porphyra yezoensis* which inhibits the oxidative liver injury of acetaminophen induced rats and the cell apoptosis of their liver cells.

BACKGROUND ART

Recently, various physiological chemistry effects of sea algae have been verified and the interest on sea algae inducing bioactive materials has been increased. Also, a cancer cell inhibition effect and lipid metabolism improvement effect in blood on ethanol extracts extracted from sea weed fusiforme, sea tangle, brown seaweed, seaweeds, green layer have been reported. In case of porphyran with the highest farm production amount of sea algae in Korea, it has the lowering action of cholesterol, antibacterial effect, anticancer effect as well as various physiological actions such as anti-coagulation effect and anti-oxidation effect of fucoidan.

Porphyra called as layer is classified as sea algae of bangiaceae of bangiales of rhodophyta and has a long ellipse shape or an egg shape like a strip with length of 14~25 cm and width of 5~12 cm. There are *Porphyra tenera, P. yezoensis, P. suborbiculata* and the like as the kind of seaweed and *P. yezoensis* is the main kind of farm seaweed in Korea. Seaweed contains in special calcium and phosphorus abundantly. As mentioned above, it is discovered that porphyran contained in seaweed as polysaccharide has bioactive effects such as anti-cancer, anti-virus and anti-coagulation actions and the like and accordingly, the great concern is concentrated to search bioactive materials of seaweed. Also, polyphenol as the antioxidation substance is contained into seaweed. Han et al. (J. Korean Soc. Food Sci, Nutr. 33, 324-330, 2004) describes that layer extracts recovers the production of pyridinoline for mixing and crosslinking collagen. Yashizawa et al. (Bioscience Biotechnology and Biochemistry 59, 1862-1866, 1995) also describes that polysaccharide extracted from seaweed shows the microphage promotion action. A study on the structure and function of porphyran extracted from various seaweed has been performed actively.

Acetaminophen (AAP) is the most-widely used anti-inflammatory agent and when taking an excess of quantity, a secure liver damage is occurred. In the United States and United Kingdom, the liver injury due to AAP occupies the highest position among causes of liver disease due to medicines. Accordingly, the liver injury mechanism caused by AAP examines closely and several studies for preventing or recovering the liver injury have been progressed. Cathleen et al. (TOXICOLOGICAL SCIENCES 84, 201-208, 2005) report that when administrating AAP into a rat, the PARP activity as one of cellular death phenomena is shown. Tamara et al. (TOXICOLOGICAL SCIENCES 76, 229-236, 2003) report that AAP generates the lipid peroxidation of liver and then causes to happen the liver injury. On the other hand, Sidhartha et al. (Archives of Biochemistry and Biophysics 369, 42-58, 1999) report that the cell apoptosis of liver cells by AAP is prevented when proanthocyanidin as grapestone extracts is administrated into a rat. Francisco et al. (Journal of Ethnopharmacology 98, 103-108, 2005) report that when administrating protium heptaphyllum extracts which has been used for a long time in South America as folk remedies, the liver injury by AAP can be prevented.

Accordingly, inventors of the present application provide with the present invention in which the liver injury induced by acetaminophen is prevented and treated by using protein extracts from *porphyra yezoensis* separated from *porphyra yezoensis* and then a mechanism on these effects is produced.

DISCLOSURE OF INVENTION

Technical Problem

An object of the present invention is to provide a composition for preventing and treating acetaminophen induced liver injury comprising the protein extracts from *porphyra yezoensis*.

Another object of the present invention is to provided an acetaminophen induced liver injury inhibition effect mechanism of the composition.

Technical Solution

The objects of the present invention are achieved as follows: sugar is removed from hot water extracts of *porphyra yezoensis*, then protein only is extracted by using ammonium sulfate, then the extracted protein is separated and purified by using column chromatography and HPLC, thereafter pure protein of 14 kDa is recovered, the seaweed protein is administrated into a white rat and a liver cell so that the liver injury inhibition effect due to AAP and the mechanism are inspected.

Advantageous Effects

The present invention relates to a composition for preventing and treating the acetaminophen induced liver injury comprising the protein separated from *porphyra yezoensis*. The protein of sodium dodecyl polyacrylamid gel electrophoresis manner measurement molecular weight of 14 kDa separated and purified from hot water extracts of *porphyra yezoensis* has an excellent effect for inhibiting the oxidative injury of the liver tissue of the acetaminophen induced rat and the cell apoptosis of their liver cell. Accordingly, since the composition of the present invention can be used to treat the liver injury prevention and treatment, the present invention is a very useful invention in the medical industry.

BRIEF DESCRIPTION OF THE DRAWINGS

The patent or application file contains at least one drawing executed in color. Copies of this patent or patent application publication with color drawing(s) will be provided by the office upon request and payment of the necessary fee.

BEST MODE FOR CARRYING OUT THE INVENTION

The present invention comprises a protein separation and purification step in the hot water extracts of *porphyra yezoensis* and a step for investigating the liver injury inhibition effect by AAP and its mechanism after administrating seaweed protein into a white rat and a liver cell.

The present invention provides a composition for preventing and treating acetaminophen induced liver injury containing the protein of sodium dodecyl polyacrylamid gel electrophoresis manner measurement molecular weight of 14 kDa separated and purified from hot water extracts of *porphyra yezoensis* as an effective component.

The effective amount of the composition of the present invention is administrated by 100 mg per 1 kg of body weight a day.

In the following descriptions, enforcement and experiments of the specific compositions and functions of the invention are explained in greater detail. However, the descriptions below aim only to present examples of the invention, and it does not mean that the rights and criteria of the invention are only limited to the following examples.

EXAMPLE

Example 1

Separation and Purification of the Protein from *porphyra yezenosis*

80 g of *porphyra yezoensis* is submerged into 2 L of distilled water, then extracted for 3 hours at 80° C., thereafter, decompressed, and filtrated by a buchner funnel. Thereafter, ethanol of the volume by three times is added into filtrated materials and then the precipitated sugar is removed, the remaining upper layer solution is obtained and concentrated by the pressure reducing manner. Thereafter, ammonium sulfate is added into the concentrated solution in order to have 80% of the final concentration thereof and then the solution is agitated for 24 hours at 4° C. in order to make the protein adsorb. Thereafter, the upper layer is removed by a centrifugal separation manner (8,000 rpm, 4° C., 20 minutes) and the ammonium sulfate with the adsorbed protein is melted by dehydrated ion water of about 20 ml. Thereafter, a dialysis process is performed (Spectra/Por membrane MWCO 3,500). Dialysis solution is loaded into a column filled with sephadex G-75, then eluted by PBS, and thereafter a peak showing the maximum value at 280 nm is confirmed (FIG. 1(A)). The confirmed fraction is concentrated by vacuum, melted into the deionized water containing TFA (Trifluoroacetic acid) of 0.1%, and separated again by HPLC. The protein peak represented at 280 nm is confirmed by using reverse-phage asahi-pak C4P column (4.6 mm×250 mm, 5□ of the particle size, Asahi Chemical Corp. Japan), the acetoacryl concentration within 0.1% of TFA is changed from 0 to 50%, eluted for 30 minutes with the of a moving fluid of 0.8 ml/min (FIG. 1(B)).

The molecular weight of the eluted sample through the above process is processed by the electrophoresis manner by means of 12.5% SDS-PAGE and thereafter confirmed by means of kumasi blue dyeing and silver dyeing.

Figure 1:
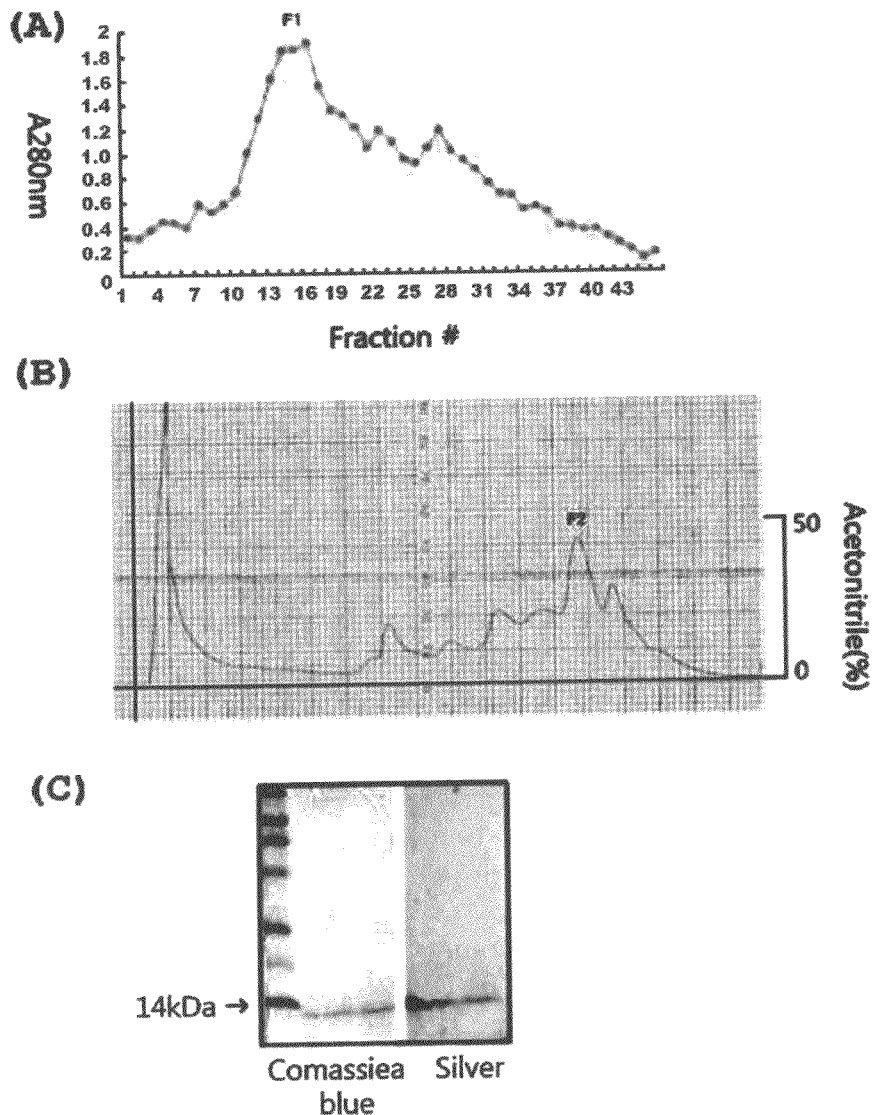
FIG. 1 shows a result (A) in which the protein is separated from *porphyra yezoensis* by using the G-75 column chromatography, an HPLC execution result (B) of fraction including protein in reverse asahi pack C4P-50 C4 column of sephadex G-75, and a dyeing result (C) of fraction including the separated protein.

As shown in FIG. 1(C), the separated and purified seaweed protein has been confirmed as a single band with the molecular weight of 14 kDa. In the present invention, the protein of 14 kDa is applied to an effect experiment about the liver injury.

Example 2

Experiment on the Liver Injury Inhibition Effect of the Seaweed Protein

The effect on the acetaminophen induced liver injury of the separated and purified seaweed protein in the above example 1 is examined by means of a rat.

Animals for the experiment are male rats (body weight of 100±10 g), as Sparague Dawley of four-week-old, obtained from Hyochang science. 10 rats are divided into three groups, respectively (control group, AAP sole administration group and AAP+seaweed protein administration group), bred in row breeding cages for 7 days as a domestication preparation breeding. At this time, the temperature (22±1° C.), humidity (50±10%) and brightness (12 hours, 08~18:00) of a breeding room are strictly controlled. After performing the domestication preparation breeding, general feed and water are freely supplied and then a saline solution (control group and AAP sole administration group) and the seaweed protein are orally administrated for two weeks. 700 mg/kg of AAP melted by DMSO is administrated into the abdominal cavity and after 24 hours, heads of rats are cut and then a blood-gathering process is performed. Each blood sample is left for 1 hour in ice water, and separated by the centrifugal device (3,000 rpm, 15 minutes, 4° C.). Thereafter, the obtained serum is preserved at the low temperature (−70° C.) and used to the experiment. And the liver is extracted and washed by the saline solution and thereafter the weight thereof is measured and a part thereof is fixed into the bouin solution (picric acid:formalin:glacial acid=15:5:1).

The assay result of the animal experiment is represented by using the mean value and the standard deviation (mean±S.D.) by each group. All data is processed by using an SPSS program for windows (Statistical Package for Social Science, SPSS Incorporation, Chicago, Ill., USA.) and an ANOVA test and Duncan's multiple range test are applied by the repetitive measurement. At this time, it is examined at the level of the statistical meaningness of $P<0.05$.

Experimental Example 1

Influence on the Liver Tissue, Liver Weight and Change of Body Weight of the Seaweed Protein To examine the influence on the liver tissue, liver weight and the change of body weight of the seaweed protein separated and purified at the example 1, the liver tissue of a rat is extracted and its weight is measured.

For this, the liver tissue of the white rat bred by each experiment group is extracted and lightly washed by the saline solution so that blood is removed. A portion of the liver tissue is cut and then the cut liver tissue is cut into thickness of 0.5 cm and fixed into Bouin fixation solution. Thereafter, the cut liver tissue is inserted into a tissue capsule within 24 hours by using the same fixation solution and fixed again. Thereafter, the fixed tissue is washed, inserted into an autotechnicon, dehydrated in the sequencing concentration alcohol and processed transparently by xylene. At an embedding center, paraffin is infiltrated into the tissue capsule and an embedding process is performed, so that a block is manufactured. The block is cut thinly with thickness of 5□ by a rotary microtome and the cut blocks are left in a floating thermostat in order to be spreaded fully and then attached onto a clean slide glass. Thereafter, to firmly adhere the slide glass and the tissue cut pieces, the slide glass with the tissue cut pieces is left at a slide warmer maintaining temperature of about 60° C. Finally, to basically observe the arrangement of cell and the morphological change, all tissue pieces are dyed by Hematoxylin & Eosin capable of separately seeing the nucleus and cytoplasm and thereafter, observed by an optical microscopy.

TABLE 1

|  | Control Group | AAP | AAP + S.E. |
|---|---|---|---|
| Initial body weight(g) | 92 ± 4.40 | 287 ± 9.09 | 94 ± 4.80 |
| Final body weight(g) | 94 ± 4.15 | 299 ± 14.92 | 281 ± 15.51 |
| Change of body weight(g) | 194.81 ± 7.1 | 205.07 ± 14.7 | 186.87 ± 15.5 |
| Weight of liver(g) | 9.41 ± 0.6 | 10.86 ± 0.9 | 9.5 ± 0.9 |

Each value represents the mean±standard deviation of 10 rats per each group.

As shown in Table 1, the change of weight and the liver weight of a white rat bred for 3 weeks do not represent the meaningful difference at the control group, AAP sole administration group and seaweed administration group.

According this, the obtained result is opposed to the result of the previous thesis (Valentovic et al., 2004) in which in the AAP administration rat, although there is no change of weight after 4 hours from administration, the liver weight is increased. Although Valentovic et al. reported that the body weight and liver weight are measured after 500 mg/kg of AAP is administrated into a rat by once, so that the result is obtained, in this experiment system that 700 mg/kg of AAP is administrated into a white rat, there is no the change of body weight and liver weight as shown in Table 1. This is considered that since in case of the AAP administration group, the AAP is administrated by once as an acute form, there is no change. In the seaweed protein administration group, the difference dose not represent in comparison with the control group 1 like the AAP sole administration group and this result is considered that the seaweed protein does not influence on the body weight and liver weight in any way and so the seaweed protein does not represent any sort of toxicity.

Figure 2:
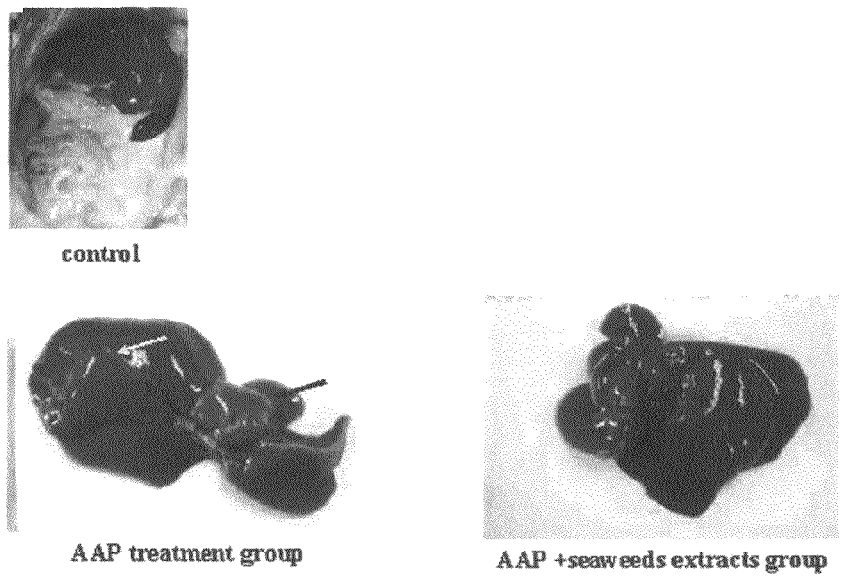
FIG. 2 shows photographs illustrating the degree of the liver injury of a rat in three experiment groups (control group, AAP sole administration group, and seaweed protein administration group).

FIG. 2 shows the degree of liver injury due to the AAP abdominal administration. The control group represents the clear scarlet, whereas the liver tissue represents the bright brown in the AAP sole administration group and black points are observed in several places. However, in the seaweed protein administration group, the clear scarlet is represented as like as the control group.

Figure 3:
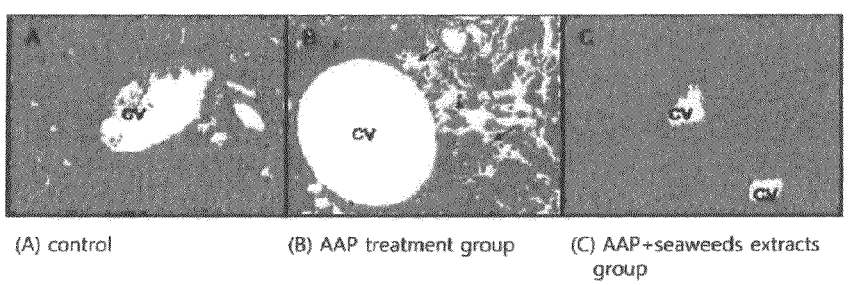
FIG. 3 shows photographs observing the inside of the liver tissue of a rat by an optical microscopy through H & E dyeing, which an arrowhead shows a DNA fragmentation state and an arrow shows a hollowing state.

The inside of the tissue is observed by an optical microscopy through H&E dyeing and as a result, as shown in FIG. 3, the plural nucleus decomposition positions are observed about the central vein at the AAP sole administration group in comparison with the control group and this means the liver cell apoptosis due to the AAP toxicity. On the other hand, in the seaweed administration group, the phenomenon represented at the AAP sole administration is reduced.

Experimental Example 2

GOT and GPT in Serum

GOT and GPT in the serum as liver function indicators are enzymes which reflect the change and necrosis of the liver cell and spilled in great quantities in the blood when damaging the liver tissue. GOT/GPT in the serum are measured by using a kit for measuring GOT (Glutamic oxaloacetic transaminase) and GPT (Glutamic pyruvic transaminase) activity measuring serum transaminase (Shinyang Chemistry, Republic of Korea) manufactured by Retiman-Frankle's manner through a spectrum photometer (Ultrospec 2001 pro. amersham phamasia biotech, United Kingdom) at 505 nm and then the result is shown in FIG. 4.

Figure 4:
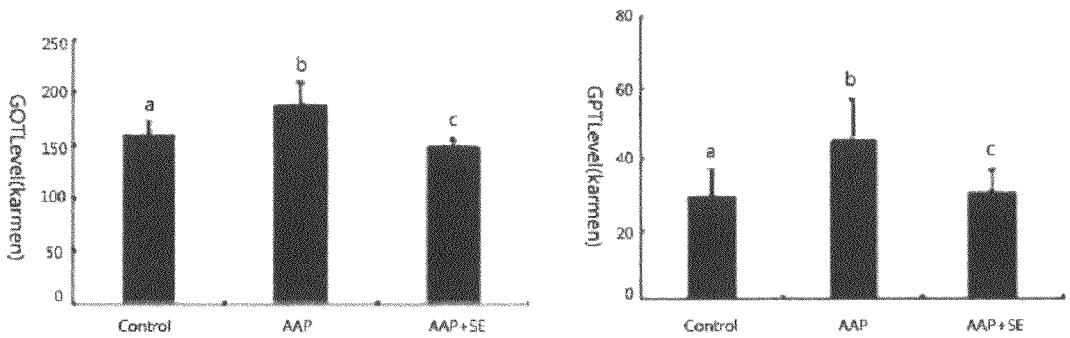
FIG. 4 shows graphs illustrating GOT/GPT values in the blood serum extracted from three experiment groups (control group, AAP sole administration group, and seaweed protein administration group).

As shown in FIG. 4, it is known that GOT is meaningly increased ($p<0.05$) in comparison with a control group (158.97±13.4 karmen) when administrating AAP (187.95±20.7 karmen) and the value of GOT is reduced below that of the control group by the seaweed protein (148.41±6.66 karmen).

On the other hand, the measuring result of GPT shows a similar tendency to GOT and that is, GOT is reduced to a similar level to the control group (28.83±7.9 karmen) at the seaweed protein administration group (30.22±6.6 karmen) in comparison with the AAP sole administration group (44.83±11.7 karmen).

Accordingly, it is considered that the GOT/GPT concentration increased by the AAP administration is recovered into the level of the control group by the seaweed protein, so that the liver injury is inhibited.

Experimental Example 3

Change of Glutathione Content in the Liver Tissue

AAP has been used as a pain-killing drug and is metabolized in the liver, so that NAPQI (N-acetyl-ρ-benzoquinoneimine) is produced as the metabolite. The metabolite is excreted as bile or urine in case that there is plenty of GSH (Glutathione) and however, in case of AAP overdose, GSH is reduced and NAPQI is combined with the liver cell protein, so that the cell injury is generated.

Accordingly, the GSH activity in the liver tissue is measured. For this, the liver tissue is homogenized by 5% of sulfosalicylic acid, then frozen by the liquid nitrogen and thereafter a thaw process is executed repeatedly by twice in a cistern of 37° C. Thereafter, the defrosted liver tissue is left for 5 minutes At 4° C. and centrifuged at 4° C., 1,000×g, for 10 minutes, so that the upper solution is obtained. The upper solution and the standard solution within the GSH assay kit are divided into a 96-well plate, respectively, thereafter a working mixture is added to the 96-well plate, and a reaction is progressed at the room temperature for 5 minutes. After 5 minutes, NADPH is inserted into the above plate and mixed through a pipet and then the absorbance is measured by the interval of 5 minutes at 412 nm.

Figure 5:
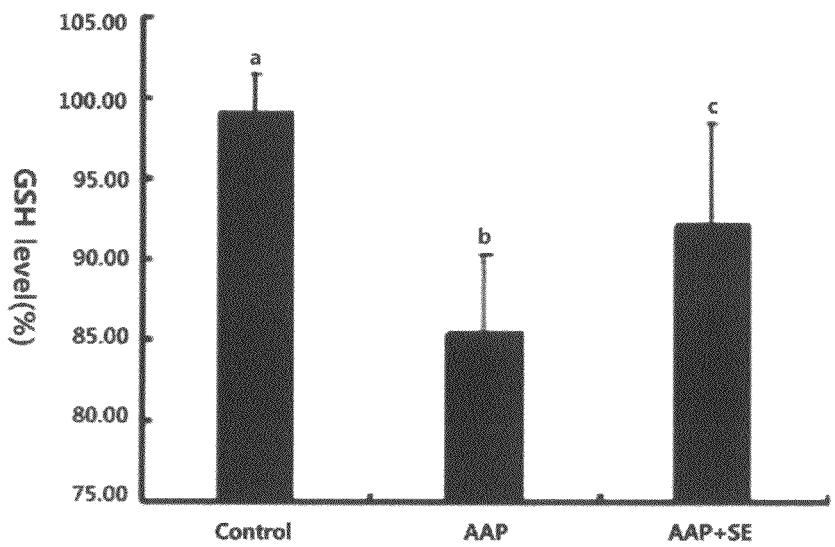
FIG. 5 shows a graph illustrating the glutathione concentration measurement result within the liver tissues of rats in three experiment groups (control group, AAP sole administration group, and seaweed protein administration group) in which a, b, and c represented to each value show the meaningful difference (a>c>b) between each group by the Duncan's multiple range test (p<0.05).

As shown in FIG. 5, the AAP sole administration group shows 85.39±4.81% of the GSH content (compares with the control group of 100%) which reduces meaningfully in comparison with the control group and however, in case that the seaweed protein is administrated into the above AAP sole administration group, the GSH content is again recovered into 92.16±6.36%. That is, the glutathion content reduced by AAP is increased by the seaweed protein, so that the liver injury due to the oxidative stress generated by AAP is inhibited.

Experimental Example 4

Change of Caspase-3 Activity and DNA Fragmentation in the Liver Tissue

The cell apoptosis is an expected death and important to maintain homeostasis of the tissue. Many studies relating to modes of cell apoptosis by AAP have been reported and however, a definite conclusion between the cell apoptosis as the natural death of a cell and the necrosis is not reported still up to the present.

Accordingly, to confirm the cell apoptosis when generating the liver injury by AAP, the activity of the caspase-3 is measured. For this, the liver tissue is homogenized by the lysis buffer (25 mM HEPES, pH 7.5, 5 mM EDTA, 2 mM DTT, 0.1% CHAPS) containing the protease inhibitor and centrifuged by 14,000×g at 4° C. The protein concentration of the obtained upper solution is measured by a BCA protein assay kit. Thereafter, 80☐ of protein is inserted into the 96-well, then the DEVD-pNA substrate is inserted, thereafter, a reaction is progressed for 4 hours at 37° C. The absorbance is measured at 405 nm.

Figure 6:
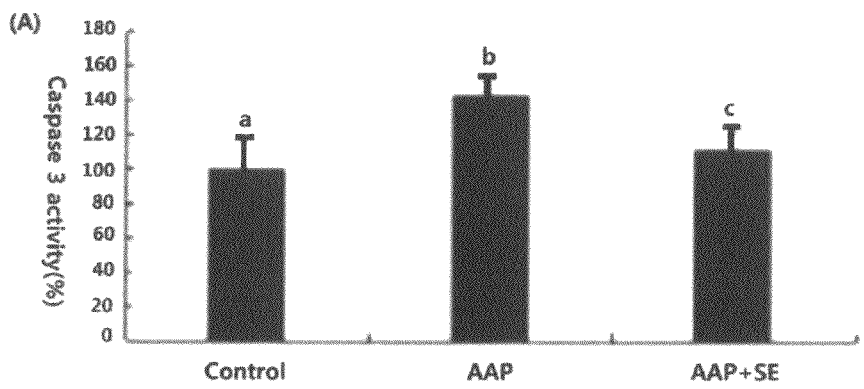
FIG. 6(A) shows a graph illustrating the caspase-3 activity measurement result in order to check the cell apoptosis when generating the liver injury by AAP, which a, b, and c marked at each numerical value show the meaningful difference (p<0.05) between the individual groups by the Duncan's multiple range test (a>c>b).
FIG. 6(B) shows a result illustrating the degree of fragmentation of the DNA extracted from the liver tissue in order to check the kind of the cell apoptosis, which lanes of 1-2 show control groups, lanes of 3-4 show AAP sole administration groups of 700 mg/kg, and lanes of 5-6 show AAP and seaweed protein administration groups.
Figure 6:
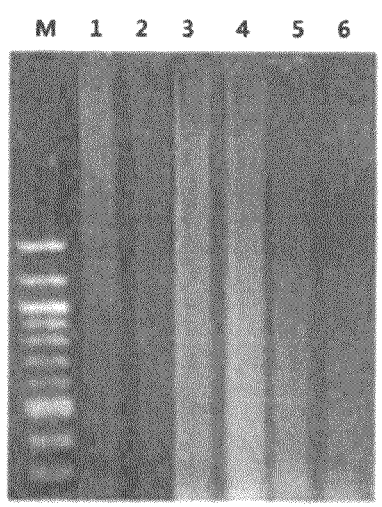

As shown in FIG. 6(A), in the AAP sole administration group, the activity of the caspase-3 is increased (143.38±10.25%) in comparison with the control group (100%), whereas the activity of the caspase-3 is again increased to 112.21±11.52% by the seaweed protein treatment.

To confirm the modes of the cell apoptosis, DNA within the liver tissue is extracted and then the degree of fragmentation is examined. As a result, as shown in FIG. 6(B), a certain DNA fraction is observed in the AAP sole administration in comparison with the control group, whereas in the seaweed protein administration group, the DNA fraction can not be observed in comparison with the AAP sole administration group.

As the above results, it is confirmed that the cell apoptosis is generated through the apoptosis mode when generating the liver injury at the white rat and it is also considered that the effect for inhibiting the cell apoptosis is represented by the protein extracted from hot water extracts of *porphyra yezoensis*.

Experimental Example 5

Examination about Proliferation and Toxicity of the HepG2 Liver Cell by the AAP Treatment Since HepG2 grows up by the same metabolism as the normal liver cell, it is generally used to an experiment relating to the toxicity and recovery of the liver by using a cell. In the above experiments, the toxicity of the liver which is represented at the white rat when administrating AAP is recovered by the seaweed protein. According this, by means of the HepG2 liver cell, the influence on the cell apoptosis by AAP and the cell proliferation inhibition effect are examined and the activity of caspase-3 by AAP inducing the cell apoptosis is measured in order to examine the liver toxicity recovery mechanism by the seaweed protein.

The used HepG2 liver cell is distributed by ATCC (American Type Culture Center).

Antibiotics (penicillin/streptomycin) of 100 units/ml is added to an MEM medium and then filtrated by a filter of 0.22☐. Before the culture, FBS (Fetal bovine serum) is added, thereby obtaining the final concentration of 10%. The cell is cultured in a 5% $CO_2$ incubator at 37° C. During the culture of the cell, the medium is replaced by twice a week and when the medium is a confluent state, the medium is washed by PBS (Phosphate Buffered Saline). Thereafter, the attached cells are separated by 0.05% of trypsin solution and centrifuged, then each cell is mixed, dispersed properly by using a pipet and divided identically.

To examine the cell proliferation and the toxicity, the HepG2 liver cell is controlled by concentration of $5 \times 10^4$ cells/ml, and divided into 96-well microplates (palcon, USA) by 100☐ per a well and cultured. After 24 hours, a medium is replaced with a serum free medium and then cultured again for 24 hours. A protein sample is dissolved into the serum free medium, then diluted until 0.01% concentration. The dilution solution by each concentration is added to each cell line and cultured for 24 hours at the 5% $CO_2$ incubator at 37° C. Thereafter, MTS/PMS solution (CellTiter 96 AQueous Non-Radioactive Cell Proliferation Assay Kit, promega corporation, USA) is processed by 10☐ and cells are cultured for 10~20 minutes. Thereafter, the absorbance at 490 nm is measured by using an automatic ELIZA reader and the cell survival ratio is calculated by a calculation formula 1. All experiments are repeatedly executed by three times.

$$\text{Mean Survival Ratio}(\%) = \frac{\text{absorbance of sample treatment group}}{\text{absorbance of control group}} \quad \text{[Calculation formula 1]}$$

To examine the toxicity of the liver cell by the AAP treatment, the activity of LDH is measured. That is, 100□ per a well with the concentration of 2×10⁴ cells/ml is divided into 96-well microplates (palcon, USA) and cultured. After 24 hours, a medium is replaced with an MEM medium including 1% FBS, then cultured again for 24 hours, and thereafter treated by an assay medium of 100□ and AAP 100□ (10, 20 and 40 mM). The obtained upper solution of 100□ is moved into a new 96-well microplate, then 100□ of the reaction mixture (solution I 250□+solution II 11.25□) is added to the new 96-well microplate. Thereafter, at the state that the light is intercepted by foil, a reaction is progressed for 30 minutes at 15~25° C. Thereafter, the absorbance at 490 nm is measured by using an automatic ELIZA reader.

Figure 7:
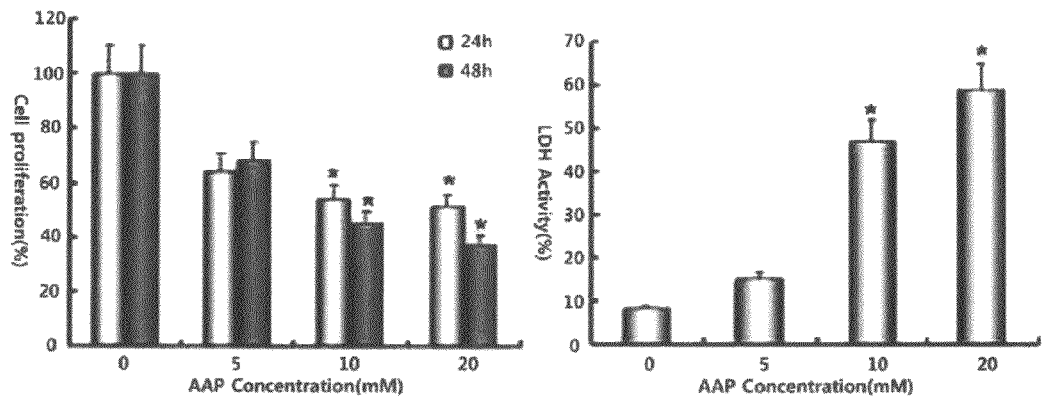
FIG. 7 shows graphs illustrating a result that AAP is treated by concentration and then the cell proliferation and toxicity of the cultured HepG2 liver cell are examined (*p<0.05).

To measure the cell proliferation inhibition effect of AAP at the HepG2 liver cell, AAP is added to a serum free medium, cultured for 24 hours and 48 hours, abd thereafter the MTT assay is executed. As a result, as shown in FIG. 7, it is confirmed that the proliferation of the liver cell is inhibited according to increase of the AAP concentration and the culture time. Also, the activity of LDH capable of securing the degree of the liver cell injury is increased in proportion to the AAP concentration, so that it can be known that the liver cell injury is included by AAP and the growth of the liver cell is inhibited.

Experimental Example 6

Cell Apoptosis of the Liver Cell Line by AAP

The cell apoptosis is a phenomenon that a suicide mechanism which inherently exists in the cell is activated by the external stimulus and then the cell died by itself as planned. The cell apoptosis differs the neurosis of a cell, that is, since the content of the cell is not isolated to the outside of the cell, it does not influence to another cell. Morphologically, the phagocytosis is progressed together with the specific gravity reduction of the cell, the destruction of the cell membrane, the condensation of chromosome, and the formation of an apoptotic body. In biochemistry, the DNA fragmentation that the DNA of chromosome is cleaved from a large piece to a small piece is generated.

Accordingly, to confirm that the cell proliferation inhibition effect by AAP is a phenomenon by the cell apoptosis, the cell with AAP and cell with no AAP are washed by PBS by means of the characteristics in which only DNA within the cell nucleus, especially, only the cell apoptosis DNA is dyed. Thereafter, the cells are dyed by the DAPI solution and then observed by a fluorescent microscopy.

Specifically, the HepG2 cell treated by the seaweed protein is washed by PBS, fixed at the room temperature for 10 minutes by 3.7% of paraformaldehyde, and dyed by means of the 4,6-diamindino-2-phenylindole (DAPI)(sigma) solution as fluorescent materials for 10 minutes. These cells are again washed by twice and the form change of the nucleus thereof is compared with that of the normal group by means of a fluorescence microscope.

To examine the DNA fragmentation phenomenon, the seaweed protein purified by the example 1 is added to the liver cell by concentration (0~100□/□), then cultured for 24 hours, and thereafter mixed with the homogenate (nuclear lysis buffer, 100 mM NaCl₂, 40 mM Tris-Cl, pH 7.4, 20 mM EDTA, 0.5% SDS). After crushing the cell, the cell is treated by RNase A and Proteinase K so that the RNA and protein are removed. The DNA condensed by the sediment of isopropanol is washed by 70% of ethanol and then dried. Thereafter, the TE buffer solution (10 mM Tris-HCl, 1 mM EDTA, pH 8.0) is applied to the dried DNA so that the DNA pellet is dissolved and then the absorbance is measured by a spectrum microscope (amersham pamatech) of 260 nm and 280 nm so that an amount of the DNA is measured. 10□ of DNA is treated by an electrophoresis manner (50V, 2 hours) in the agarose cell, dyed by editium bromide, and measured by means of ultraviolet rays and the like.

Figure 8:
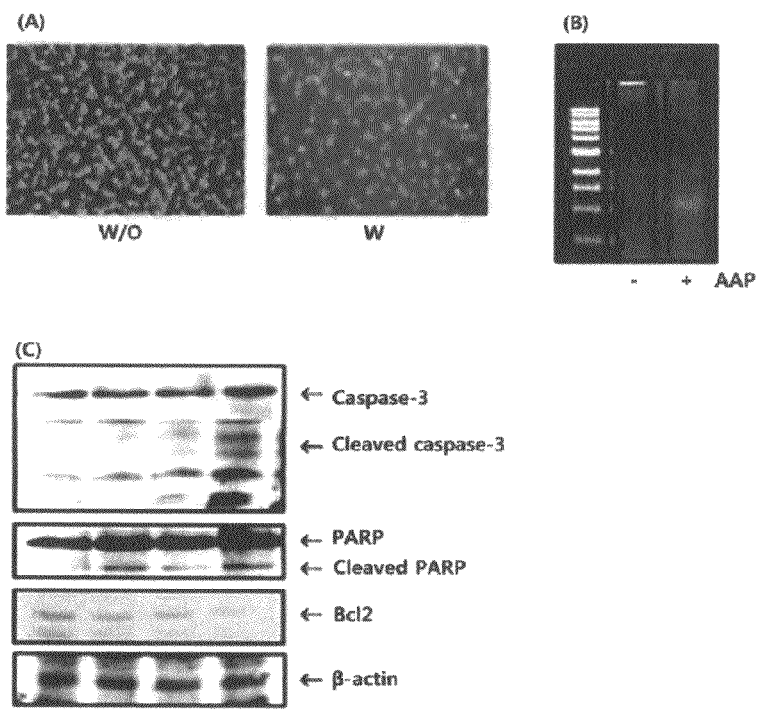
FIG. 8(A) shows the morphological change by using a DAPI dyeing manner.
FIG. 8(B) shows fragmentation of DNA.
FIG. 8(C) shows the change of pro-apoptotic molecules during AAP induced cell apoptosis.

As shown in FIG. 8, in case of the culture for 24 hours by adding AAP, it is confirmed that not only the number of cells is reduced and but also many cell apoptosis modes with the red color are formed. The DNA fractions are confirmed identically.

The cell apoptosis is represented as the signal transmission through a receptor of the cell surface and the activation of the caspase family through Bax and Bcl-2 of mitochondrion. A chain of processes of the cell apoptosis signal transmission is performed nearly by the protein interaction. There are Bcl-2, Bcl-X and Bcl-W as the representative proteins for inhibiting the cell apoptosis and there are also Bax, Bad, and Bak and the like as the representative proteins for promoting the cell apoptosis. It is known that the balance between these proteins performs an important role for controlling the cell apoptosis.

Through the above results, since it is confirmed that the cell apoptosis of the liver cell is induced by AAP, the liver cell is treated by means of AAP according to the concentration and the western blot is executed to observe the expression modes of the protein related to the cell apoptosis.

For this, a cell is cultured at a culture dish of 100-mm diameter until it become a confluent monolayer of a confluent state by a medium containing 10% FBS. Thereafter, the medium is replaced with a serum free medium and cultured for 24 hours. After 24 hours, each sample is treated by a serum free medium added according to the concentration and cultured for 24 hours. The culture solution is removed, then washed by the cold PBS solution, and thereafter the cell is recovered through the cell lysate buffer solution containing 1% triton. After the centrifugal process, 4× Laemmli sample buffer (13.3% SDS, 0.4M Tris, 0.013% bromopheno blue, 40% glycerol, pH 6.5) is added to the obtained upper layer solution by 1× of concentration and then an electrophoresis manner is performed in 12.5% SDS-polyacrylamid gel by means of Mighty Small II Apparatus (Hopper Science Instruments, USA). After the electrophoresis manner, the protein separated into the gel is transferred to Immobilon-P membrane (Milipore corporation, the pore size: 0.1□, USA) by means of Semi-dry Transfer unit, Sigma, USA), reacted at the room temperature for 2 hours in 1×TBS (Tris-buffered saline; 20 mM Tris-base, 137 mM NaCl, 1M HCl) containing 1% BSA, and thereafter left for a night at 4° C. by a primary antibody. Thereafter, the protein is washed by three times at each 10 minutes by TBS-T (Tris-buffered saline, 0.1% Tween 20) and reacted at the room temperature for 1 hour together with the anti-rabbit or anti-mouse IgG-conjugated horseradish peroxide secondary antibody diluted by 1:20,000. The membrane reacted by the second antibody is washed by three times for 10 minutes by TBS-T, exposed to the X-ray film by means of Super signal west pico stable peroxide solution and Super signal west pico luminol/enhancer solution and then each protein is confirmed by a band. At this time, Bcl-2, PCNA (Proliferating Cell Nuclear Angigen), caspase-3, cleaved caspase-3, PARP (Poly ADP-ribose Polymerase), cleaved PARP, and β-actin antibody related to the cell apoptosis are used a the primary antibody.

As shown in FIG. 8, when the liver cell is treated by AAP, the caspase-3 with inactivity is cleaved and then the activity is increased. According to increase of the cleaved caspase-3, PARP for treating the DNA injury existing within a nucleus is cleaved from 116 kDa to 85 kDa so that an inactivity state of PARP is generated. Additionally, the expression of Bcl-2 for inhibiting the cell apoptosis is inhibited according to the increase of the AAP concentration. Through this result, it is considered that the liver cell injury by AAP would be related to the cell apoptosis.

Experimental Example 7

Liver Cell Injury Inhibition Effect by AAP of Seaweed Protein

Through the above results, it is confirmed that the cell apoptosis of the liver cell is induced by the increase of the AAP concentration and accordingly, the seaweed protein and AAP are processed together and the liver injury inhibition effect of the seaweed protein by AAP is confirmed.

At first, the degree of the PCNA protein expression capable of securing the recovery of the injured cell is confirmed. For this, a liver tissue is homogenized by lysis buffer (25 mM HEPES, pH 7.5, 5 mM EDTA, 2 mM DTT, 0.1% CHAPS) containing the protease inhibitor and then centrifuged by 14,000×g at 4° C. Thereafter, the protein concentration of the obtained upper layer solution is measured by means of a BCA protein assay kit. A loading process is performed by 50□ per each lane, an electrophoresis process is performed by SDS-PAGE, and thereafter it is moved toward the PVDF membrane (Millipore, USA). At this time, the rainbow molecular marker (amersham) is used as the standard molecular weight. In the separated protein, the expressin of the caspase-3 protein is confirmed by means of Super Signal West Pico Chemiluminescent Substrate (pierce biotechnology incorporation, USA). Thereafter, a blocking process is performed for 2 hours in Tris-buffered Saline (10 mM Tris-HCl, 150 mM NaCl, pH 7.5) containing 0.1% Tween 20 and thereafter the washing process is performed by twice for 15 minutes by means of TBS-T (Tris-buffered Saline containing 0.1% Tween 20).

The washed membrane is reacted for a night at 4° C. in caspase-3 primary antibody (Anti-capase 3 polyclonal rabbit IgG, santacruse biotechnology incorporation) diluted at TBS-T by 1:500. The membrane washed by twice for 15 minutes by means of TBS-T is reacted for 2 hours by peroxidase labelled anti-rabbit antibody (1:10000) and thereafter washed again by twice for 15 minutes by means of TBS-T. Thereafter, it is exposed to the KODAK X-ray by means of Super Signal West Pico Stable Peroxide Solution and Super Signal West Pico Luminol/Enhancer solution. After developing the X-ray film, a band is confirmed by means of densitometer and Science Lab 2005 (Fuji Film).

As a result, the expression of the PCNA protein related to the cell recovery and proliferation is increased according to the increase of the treatment concentration of the seaweed protein in comparison with the case that only 20 mM AAP is processed to the liver cell.

Caspase is a cystein-related protease activated by the cell apoptosis induced activation signal and related directly or indirectly to the decomposition of the many target proteins such as PARP and the like existing the cell, so that the activation of the caspase-3 is a final product capable of securing the degree of the cell apoptosis.

As described hereinbefore, when the AAP is processed to the liver cell according to the concentration, the activation of caspase-3 is increased by the cell apoptosis and the cleaved types are increased. Accordingly, to examine whether the seaweed protein inhibits the cell apoptosis by AAP, the seaweed protein and AAP are processed together and thereafter the expression degree of caspase-3 is examined.

Figure 9:
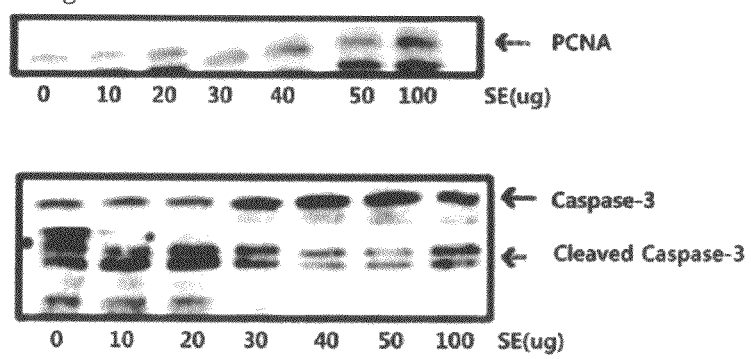
FIG. 9 shows the expression degree of caspase-3 in order to check whether seaweed protein inhibits the cell apotosis by AAP after the seaweed protein and AAP are treated together.

As shown in FIG. 9, although the activated and cleaved caspase-3 is increased in a case that only 20 mM AAP is processed to the liver cell, the cleaved caspase-3 with activation is reduced according to increase of the seaweed protein treatment concentration and the caspase-3 with inactivation is increased. That is, the cell apoptosis of the liver cell by AAP is inhibited by the seaweed protein, the caspase-3 activation is reduced. As a result, the PCNA protein expression related to the cell proliferation is increased, so that it is considered that the seaweed protein inhibits the liver cell injury of AAP.

The invention claimed is:
1. A method for treating acetaminophen induced liver injury in a subject in need thereof comprising:
administering to said subject a therapeutically effective amount of a separated and purified *Porphyra yezoensis* protein, wherein the separated and purified *Porphyra yezoensis* protein has a molecular weight of 14 kilodaltons (kDa), wherein said molecular weight is measured by sodium dodecyl sulfate polyacrylamide gel electrophoresis, and wherein the separated and purified protein is obtained by extracting *Porphyra yezoensis* with water at a temperature of 80° C. to provide an aqueous extract of *Porphyra yezoensis*, filtering the aqueous extract, adding ethanol to the filtered aqueous extract to precipitate sugar and form an upper layer, separating and concentrating the upper layer under reduced pressure, adding ammonium sulfate to provide an ammonium sulfate layer, separating and dialyzing the ammonium sulfate layer and subjecting the dialyzed layer to column chromatography to obtain the separated and purified *Porphyra yezoensis* protein.

* * * * *